United States Patent [19]

Harmer

[11] Patent Number: 4,682,889

[45] Date of Patent: Jul. 28, 1987

[54] REFRACTOMETER FOR MEASURING THE REFRACTIVE INDEX OF A LIQUID

[75] Inventor: Alan L. Harmer, Plan Les Ouates, Switzerland

[73] Assignee: Stanley Electric Co., Ltd., Tokyo, Japan

[21] Appl. No.: 720,411

[22] PCT Filed: Jul. 31, 1984

[86] PCT No.: PCT/CH84/00122

§ 371 Date: Apr. 2, 1985

§ 102(e) Date: Apr. 2, 1985

[87] PCT Pub. No.: WO85/00886

PCT Pub. Date: Feb. 28, 1985

[30] Foreign Application Priority Data

Aug. 3, 1983 [CH] Switzerland .................. 4215/83

[51] Int. Cl.$^4$ ............................................. G01N 21/41
[52] U.S. Cl. .................................................. 356/135
[58] Field of Search .......................... 356/135–137, 356/128

[56] References Cited

U.S. PATENT DOCUMENTS

| 2,319,889 | 5/1943 | Straat. | |
|---|---|---|---|
| 2,421,854 | 6/1947 | Seaman. | |
| 2,427,996 | 9/1947 | Seaman. | |
| 2,502,913 | 4/1950 | Arnulf. | |
| 3,625,620 | 12/1971 | Goldberg. | |
| 4,187,025 | 2/1980 | Harmer | 356/133 |
| 4,240,747 | 12/1980 | Harmer | 356/133 |
| 4,427,293 | 1/1984 | Harmer | 356/133 |
| 4,427,913 | 1/1984 | Iafrate et al. | 310/334 |
| 4,433,913 | 2/1984 | Harmer | 356/133 |
| 4,539,475 | 9/1985 | Bosse | 356/137 |

FOREIGN PATENT DOCUMENTS

| 2159771 | 6/1973 | France. | |
| 2250434 | 5/1975 | France. | |
| 1209036 | 10/1970 | United Kingdom. | |
| 1252766 | 11/1971 | United Kingdom. | |
| 2008793 | 6/1979 | United Kingdom. | |
| 2136593 | 9/1984 | United Kingdom | 356/135 |

OTHER PUBLICATIONS

Polymer Handbook, by J. Bandrup and E. H. Immergut, Title page only.
Plastic Optics: Reclaiming a Fine Technology, by Peter Lahaye, pp. 27–29, *Optical Spectra*, Jul. 1974.

*Primary Examiner*—F. L. Evans
*Attorney, Agent, or Firm*—Cushman, Darby & Cushman

[57] ABSTRACT

A refractometer comprises a light source (DEL), a prism (P) immersed in a liquid (L) and the entry face of which is a cylinder portion. The exit face (2) of the rays is cut according to an acute angle ($\theta$) relative to a diametrical plane (3) of the cylindrical face so that the rays refracted through the prism at two different temperatures, for a liquid of given concentration, however, emerge from the face (2) converging towards a common zone thereby tending to measure the concentration of the liquid independently of the temperature variations.

4 Claims, 3 Drawing Figures

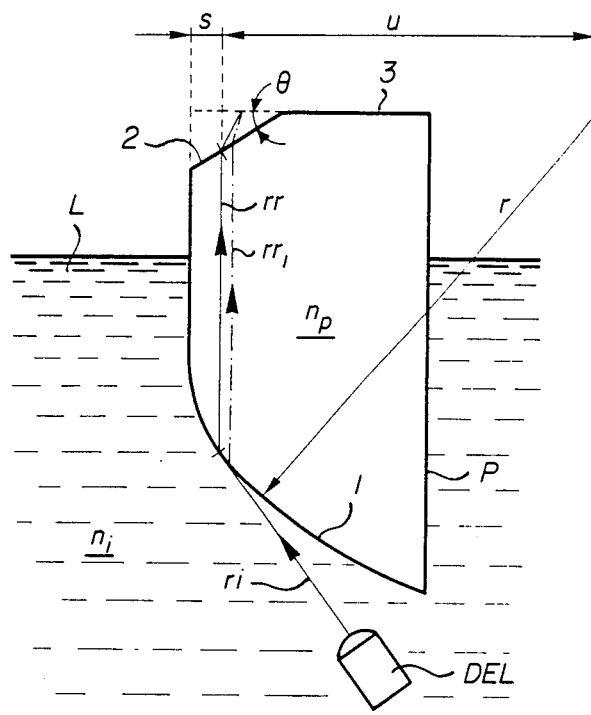
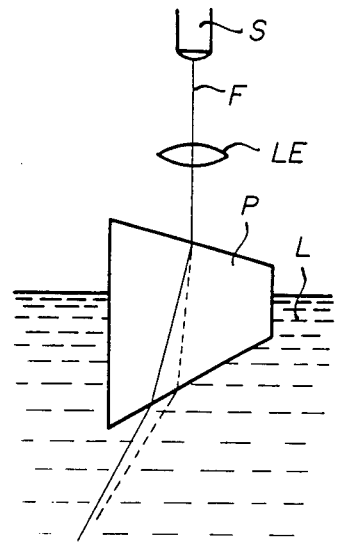
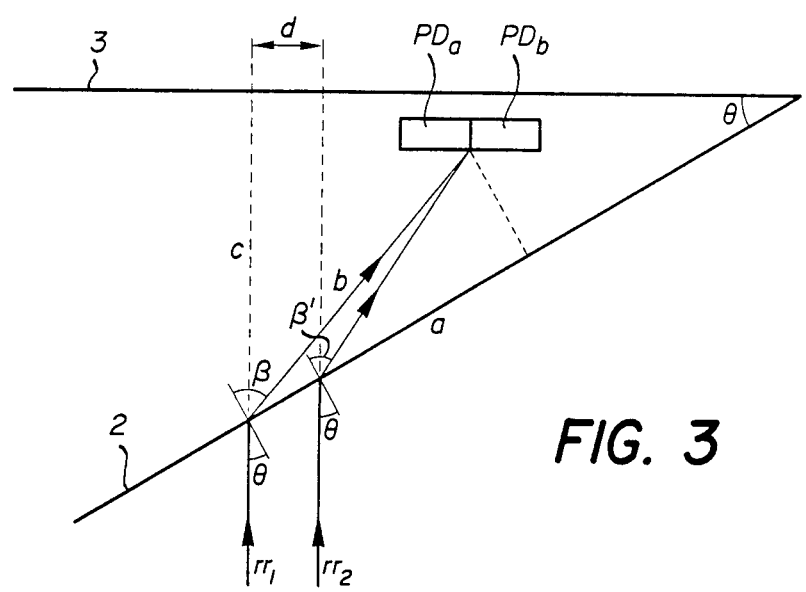
FIG. 2
FIG. 1
FIG. 3

REFRACTOMETER FOR MEASURING THE REFRACTIVE INDEX OF A LIQUID

The subject of the present invention is a refractometer for measuring the refractive index of a liquid, comprising a prism, of which at least one of the faces is in contact with the liquid to be measured, a light source to direct a light beam through the prism and passing through the said face in contact with the liquid and through one face in contact with another medium.

Refractometers of this type are well known. They usually have the characteristic feature of measuring the refractive index for a given temperature. Although this feature is acceptable when the temperature of the liquid can be controlled, it is not an accurate measure in other cases, such as those of refractometers used for indicating the state of charge of a battery as a function of the refractive index of the electrolyte of the battery.

A refractometer of this type has already been disclosed in British Pat. No. 2 008 793, having one face formed by a cylindrical portion receiving an incident light beam, in contact with the said liquid, and one exit face for light rays refracted by the receiving face and transmitted through the prism, forming along the exit face on opposite sides of a transition line an illuminated and a non-illuminated zone, the position of the transition line being a function of the refractive index of the liquid.

As explained in Optica acta 1970, vol. 17, No. 5, pp 363-380, it is possible, by means of a prism having a surface that receives a light beam comprises a cylinder portion immersed in the liquid, the refractive index of which is required to obtain on a face where the light rays emerge a clear transition line between an illuminated zone formed by the refracted part of the beam passing through the two different refractive index media, and a non-illuminated zone. The face where the light rays converge is within a plane parallel to one diameter of the cylinder perpendicular to the general direction of the refracted rays, and the position of the transition line between the illuminated and non-illuminated zones is a practically linear function of the refractive index of the liquid. This refractometer operates based on the fact that the angle of incidence of the rays of the light beam increases progressively, due to the curvature of the receiving surface, so that beyond a critical angle, the rays of the light beam are no longer refracted through the prism. This critical angle of incidence is a function of the relationship between the refractive index of the liquid and that of the prism.

All the refracted rays reach the plane of convergence to the right of a certain point which forms the boundary between the illuminated and non-illuminated zones, and the position of the line of contrast between the zones is a function of the relationship between the refractive indices of the liquid and that of the probe.

These considerations apply so long as the temperature of the liquid and the prism is known, or remains constant. When a refractometer of this type is used to determine the refractive index of the electrolyte of an electrochemical battery and in this way the degree of charge of the battery, the temperature of the electrolyte, which can vary by several tens of degrees when a car battery is involved, is not known. Consequently, it is not possible to establish a direct correlation between the refractive index measured and the state of charge of the battery.

Refractometers are known which are provided with means for compensating the temperature variations, in such a way as to measure the index of a liquid as a function of a reference temperature.

Apparatus of this type forms notably the subject of French Patent 2 159 771 and U.S. Pat. No. 3 625 620. In these two solutions, use is made of a correction mechanism using a bimetal compensation strip. Although a mechanism of this type is simple, its presence leads to complications, presupposes prior adjustment and is affected by vibrations.

The aim of the present invention is to provide a solution which is substantially free of the above-mentioned disadvantages.

To this end, the subject of the present invention is a refractometer which measures a refractive index of a liquid substantially independently of its temperature range. This refractometer includes a prism that has a plurality of faces, at least one of these faces being in contact with the liquid to be measured. A light source directs the light beam through the prism to be incident upon and passed through the face which is contact with the liquid and the face that is in contact with the other medium. These two faces form non-right angles with the incident beams at the corresponding faces. A measuring scale is located at a location where the refracted beams will converge independent of temperature for a particular liquid. The refractive index of this liquid varies as a function of its temperature, and the refractive index of the other medium also varies as a function of its temperature. However, the refractive index of this other medium is lower than that of the liquid to be measured.

The advantage of a refractometer of this type is that it provides not only linear indication as a function of the refractive index, but also indication of this index with respect to a reference temperature. As a result, in a case where the liquid comprises the electrolyte of an electrochemical battery, the refractive index is a direct correlative of the state of charge of the battery, in that the temperature parameter is almost neutralised or at least greatly reduced. The proposed solution is simple, exclusively optical and unaffected by vibrations which is particularly important in the case of its use in the field of cars.

The attached drawings illustrate diagrammatically and by way of example two embodiments of the refractometer which is the subject of the present invention.

FIG. 1 is a diagrammatic view of the first embodiment.

FIG. 2 is a diagrammatic view of the second embodiment.

FIG. 3 is a partial and enlarged view of this embodiment.

The embodiment shown in FIG. 1 will be used to more particularly explain the principle of the present invention. This refractometer comprises a prism P placed in the path of a light beam coming from a light source S and passing through a lens LE. The prism P is partially immersed in a liquid, the measurement of the refractive index of which is required.

The entry and exit faces of the prism P form non right angles with the axis of the light beam F, so that the beam is subjected to a first refraction entering the prism P and a second one leaving it. In the present case where the medium of incidence is air, the variation in the refractive index as a function of the temperature is considerably lower than that of the liquid to be measured. If the temperature increases for example, the angle of refraction of the incident beam increases less than the angle of refraction of the emergent beam of the prism, as shown by broken lines in FIG. 1. However, by selecting the dimensions correctly, the beams refracted at different temperatures meet again approximately at a given point. These conditions will be examined in greater detail in the case of the second embodiment.

The refractometer illustrated in FIG. 2 comprises a prism P of which a semi-cylindrical face 1 receives incident rays ri of a light beam from an electroluminescent diode DEL. This diode and the semi-cylindrical face 1 of the prism P are immersed in the liquid L, the refractive index measurement of which is required. The prism comprises an exit face 2 for refracted rays of the incident beam, which forms an angle $\theta$ with a convergence plane 3 of the refracted rays, parallel to a diametrical plane of the semi-cylindrical face 1 that receives the incident rays, perpendicular to the general direction of the refracted rays rr through the prism P. One portion of the incident rays ri is refracted through the prism P as a function of the relationship between the refractive index $n_i$ of the liquid and that of the prism $n_p$, forming a non-illuminated zone u and an illuminated zone s on the convergence plane 3.

We shall now examine how the length of the non-illuminated zone u varies as a function of the temperature, r being the radius of the semi-cylindrical face 1, $$s = r(n_i/n_p)$$

$$u = r - s = r[1 - (n_i/n_p)]$$

$$\frac{du}{dt} = u'$$

$$= r'[1 - (n_i/n_p)] - r(n'_i/n_p) + r(n_i/n_p^2) \cdot n'_p$$

$$u' = (r'/r) \cdot r(1 - n_i/n_p) - \quad (1)$$

$$r(n_i/n_p) \cdot (n'_i/n_i) + \quad (2)$$

$$r(n_i/n_p) \cdot (n'_p/n_p) \quad (3)$$

Let us now examine the effect of the refractive index variation of the prism as a function of the temperature for a prism, the exit face 2 of which forms an angle of zero with the plane 3, both for a prism of plexiglass (PMMA), and a prism of polymethyl pentane (TPX), both with the receiving face 1 immersed in a solution of 28% $H_2SO_4$.

For PMMA $n_p = 1.49$, $n_i = 1.365$, $n'_p = -1.3 \times 10^{-4}/°C.$,
$n'_i = 2.5 \times 10^{-4} °C.$
$r'/r = \alpha =$ dilatation coefficient $= 7 \times 10^{-5}/°C.$
$r = 24.8$ mm
Term 1 of the equation for $u' = +0.163$ $\mu m/°C.$
Term 2 of the equation for $u' = +4.16$ $\mu m/°C.$
Term 3 of the equation for $u' = -1.98$ $\mu m/°C.$ $$u' = 2.34 \ \mu m/°C. \left(\frac{dn}{dt} \sim -1.40 \times 10^{-4}/°C.\right)$$

For TPX $n_p = 1.465$, $n_i = 1.365$, $n'_p = -1.67 \times 10^{-4}/°C.$
$n'_i = -2.5 \times 10^{-4}/°C.$, $r'/r = 11.7 \times 10^{-5}/°C.$,
$r = 24.8$ mm
Term (1) of the equation for $u' = +0.198$ $\mu m/°C.$
Term (2) of the equation for $u' = +4.23$ $\mu m/°C.$
Term (3) of the equation for $u' = -2.63$ $\mu m/°C.$ $$u' = 1.80 \ \mu m/°C. \left(\frac{dn}{dt} \sim -1.08 \times 10^4/°C.\right)$$

It can be observed that the greater the value of the variation of the refractive index of the prism as a function of temperature, the less u varies.

It should be noted that term 1 of the equation is due to thermal dilatation of the prism and the values indicated relate to the centre of the ray for an independent photodiode. If the photodiode is set at a distance u directly on the prism P, it moves with the prism and there is only a secondary error less than the error indicated, which can therefore be ignored.

Table 1 below compares the temperature sensitivity of different plastics materials.

TABLE I

| | | Material 1 | | Prism only 2 | | Prism + probe 3 |
|---|---|---|---|---|---|---|
| | | Refraction index | $\frac{dn}{dT} \times 10^{-4}/°C.$ | displacement of dark/light zone($\mu m/°C.$) | equivalent $\frac{dn}{dT} \times 10^{-4}/°C.$ | $\frac{dn}{dT} \times 10^{-4}/°C.$ |
| PMMA | sheet | 1.4813 at 26° C. | −1.35 | | | |
| | rod | 1.4912 at 26° C. | −12.6 | 2.2 ± 0.5 | −1.32 ± 0.3 | −1.11 |
| TPX (ICI) | | 1.4612 at 26° C. | −1.67 | −1.1 ± 0.3 | −0.66 ± 0.2 | Probe CP4 −0.52 |
| EPOTEK No 307 | | 1.5617 at 25° C. | −1.00 | | | |
| Poly Carbonate PC (Markolan) | | 1.5857 at 23° C. | −0.92 | | | |
| PVC | | 1.5382 at 26° C. | −1.18 | 1.4 ± 0.5 | −0.84 ± 0 × 3 | |
| SUBSTRATE OF PHOTODIODE BPX48 | | 1.5707 at 24° C. | −0.80 | | | |

| | | | Published data 4 | | | |
|---|---|---|---|---|---|---|
| | | | n | $\frac{dn}{dT} \times 10^{-4}/°C.$ | $\alpha \times 10^{-5}/°C.$ | Tg (°C.) |
| PMMA | sheet | | 1.492 | −0.85 | 7 | 110° |
| | rod | | | | (5−9) | |
| TPX | | | | | | |

TABLE I-continued

| | | | |
|---|---|---|---|
| (ICI) EPOTEK No 307 | 1.465 | | 11.7 |
| Poly Carbonate PC (Markolan) | 1.586 | −1.45 | 6.6 |
| PVC SUBSTRATE OF PHOTODIODE BPX 48 | | | 6.6–7.3  70–100° |

1 Measured on a Abbe refractometer n and dn/dT.
2 Measured in a medium of refractive index 1.38 using a microscope with a graduation for observing the movement of a dark/light transition line.
3 With double PD BPX48 stuck on the prism.
4 From Polymer Handbook and "Plastics Optics" Optical Spectra, July, 1974, p.27.

Although the TPX with its highest dn/dt is the material which produces the lowest variation as a function of the temperature, it doe not allow this variation to be eliminated.

This is why the subject of the invention lies principally in a modification of the structure of the prism which consists in forming the angle $\theta$ between the exit face 2 of the prism P and the convergence plane 3 on which is mounted the scale which, in this example, relates to the state of charge of the battery.

With reference to the diagram in FIG. 2, an incident ray ri refracted through the prism is represented and, after refraction, the ray is designated by rr. This corresponds to the refraction at a first temperature $T_0$. If the temperature rises from $T_0$ to $T_1$, the same incident ray assumes the path drawn as a dot-and-dash line $rr_1$ has a result of the decrease in the refractive index of the liquid. Since there is also a reduction in the refractive index of the material forming the prism P, the sine of the angle $\beta$ which the emergent ray forms with the perpendicular at the face 2 at the point of incidence of the ray on this face, is a function of this index multiplied by the sine of the angle of incidence, so that the angle of refraction $\beta$ decreases with the increase in temperature, because the value of the refraction incidence decreases when the temperature increases.

This compensation is not total. However, it can be noted that the TPX prism, the measured value dn/dT of which (see table I) is $-0.66 \times 10^{-4}/°C.$, passes with the prism the face 2 of which forms an angle $\theta$ of 35° with the plane 3, to $-1.3 \times 10^{-5}/°C.$ This value is obtained by placing a double photodiode on the focal plane 3 of the refracted rays and by measuring the relationship R between the currents of photodiodes PDa/PDb as a function of the temperature of a solution $H_2SO_4$ of refractive index 1.3680. The average of the measured ratios gives $$\frac{dR}{dT} = 1.2 \times 10^{-4}$$

which is equivalent to an apparent refractive index variation as a function of the temperature of $-1.3 \times 10^{-5}/°C.$ If it is considered that the value dn/dT in a liquid of refractive index $n_i = 1.37$ (28% $H_2SO_4$) is $-2.5 \times 10^{-4}/°C.$, it can be noted that with a TPX probe of which the exit face 2 for refracted rays forms an angle of approximately 35° with the plane 3, the refractive index variation as a function of the temperature is 20 times lower.

Table II gives the sensitivity of the TPX prism measured at different refractive indices of the liquid using a double photodiode $PD_a$, $PD_b$ the current of which is measured in nA, the current of the electroluminesecnt diode DEL being 50 mA.

TABLE II

| Refractive index | 1.3528 | 1.3597 | 1.3680 | 1.3772 | 1.3828 |
|---|---|---|---|---|---|
| $PD_a$ | 196 | 220 | 248 | 276 | 267 |
| $PD_b$ | 440 | 430 | 430 | 415 | 395 |
| Ratio | 0.445 | 0.511 | 0.576 | 0.665 | 0.676 |

The sensitivity dR/dn of 9.1/refractive index measured here is reduced correspondingly because the double photodiode was not exactly on the focal plane of the rays refracted by face 2.

With the angle $\theta$ of face 2 with the plane parallel to the diametrical plane of the prism perpendicular to the general direction of the rays refracted through the prism selected at 35°, we shall calculate the position of the photodiode or the graduated scale relative to the point of exit on the cut face 2 of the refracted ray characteristic of the refractive index of the liquid and forming the transition line between the illuminated and non-illuminated zones.

With reference to FIG. 3, the prism in FIG. 2 has been shown partially enlarged. Its beam focussing plane 3 is partially cut to form the inclined face 2 of angle $\theta$ relative to the beam focussing plane 3. Two refracted rays $rr_1$ and $rr_2$ are shown which are characteristic of the refractive index of the liquid at 20° C. and 30° C. respectively. The distance d between the two refracted rays is greatly exaggerated to facilitate explanation. The variation of the refractive index of the TPX prism P as a function of the temperature is, according to table I, $0.52 \times 10^{-4}/°C.$ which, in the case of a prism the radius r of which is 24.8 mm, a displacement d of 0.87 $\mu$m/°C. or 8.7 $\mu$m for 10° C.

The radius r being selected like angle $\theta$, d for a variation of 10° C. being determined, parameters a, b and c should be calculated in order to determine the position of the double photodiode $PD_a$ and $PD_b$ for measuring the position of the transition line between the illuminated and non-illuminated zones, characteristic of the refractive index of the liquid in which the refractometer is immersed. This position is in a convergence zone of emergent rays from face 2 of the prism for a liquid of a given concentration, but the index of which is measured at different temperatures.

$$\frac{a + d/\cos\theta}{\tan\beta} = \frac{a}{\tan\beta'}$$

therefore $$a = \frac{d \tan\beta'}{\cos\theta (\tan\beta - \tan\beta')}$$

$$b = \frac{a}{\sin\beta} = \frac{a}{n_p \sin 3074}$$

-continued $$c = n_p b = \frac{a}{\sin \theta}$$

Table III gives both the values of these parameters and the angles of refraction $\beta$ and $\beta'$ respectively of rays refracted through the prism $rr_1$ and $rr_2$, for different angles $\theta$ of face 2.

TABLE III

| $\theta$ | $\beta$ | $\beta'$ | a (mm) | b (mm) | c (mm) |
|---|---|---|---|---|---|
| 30° | 47.167° | 47.069° | 4.08 | 5.57 | 8.16 |
| 35° | 47.272° | 57.171° | 2.69 | 3.20 | 4.69 |
| 40° | 70.520° | 70.336° | 1.12 | 1.19 | 1.74 |

I claim:

1. A refractometer for measuring a refractive index of a liquid to be measured, substantially independently of its temperature range, comprising:
   a prism having a plurality of faces, at least one of the faces being in contact with the liquid to be measured;
   light source means for directing a light beam through the prism to be incident upon, and pass through the one face and to be incident upon and pass through another face which is in contact with another medium, the one and the another faces of the prism traversed by the said beam forming corresponding non-right-angles with incident beams at the one and another faces;
   wherein the other medium has a refractive index variation as a function of a temperature thereof which is lower than a refractive index variation of the liquid to be measured; and
   a measuring scale structure, disposed in a location in which refracted light beams, refracted when passing from the liquid into the prism and when passing from the another face into the another medium, are substantially convergent;
   the refractive index of the liquid varying as a function of a temperature range simultaneously affecting the liquid and the prism having one face in contact therewith.

2. Refractometer according to claim 1, wherein said one face of the prism is formed as a cylindrical portion receiving the incident light beam in contact with the liquid, and said another face receives light rays refracted by the one face and transmitted through the prism to form an illuminated zone and a non-illuminated zone on opposite sides of a transition line.

3. Refractometer according to claim 2, wherein the prism comprises a material having a refractive index variation of which as a function of the temperature variation is greater than $-1.1 \times 10^{-4}/°C$.

4. A refractometer adapted to be at least partially inserted into a fluid to measure a refractive index thereof, comprising:
   light source means for producing a light beam;
   a prism, located in a path of said light beam and having a plurality of faces, one of the faces being in contact with the fluid to be measured, and another of the faces being in contact with a second fluid so that light beams incident upon said faces are refracted between said fluid to be measured and said one face, and between said second fluid and said another face, both of said one and said another face of said prism forming non-right angles with said light beams incident thereupon which are produced by said light source means; and
   means for measuring refracted beams which are refracted from one of said faces into one of said fluids, said measuring means located in a location where beams refracted by said prism converge substantially independently of temperature;
   wherein said fluid to be measured has a refractive index which varies as a function of temperature, and said second fluid has a refractive index which varies as function of temperature but which varies less than that of said fluid to be measured.

* * * * *